United States Patent [19]
Wu

[11] Patent Number: 6,047,429
[45] Date of Patent: Apr. 11, 2000

[54] TOOTHBRUSH WITH WATER JET

[75] Inventor: Ka Shing Wu, Hong Kong, The Hong Kong Special Administrative Region of the People's Republic of China

[73] Assignee: Addway Engineering Limited, The Hong Kong Special Administrative Region of the People's Republic of China

[21] Appl. No.: 09/169,321

[22] Filed: Oct. 9, 1998

[51] Int. Cl.[7] .................................................. A46B 13/04
[52] U.S. Cl. ................................................................ 15/29
[58] Field of Search ........................................... 15/24, 29

[56] References Cited

U.S. PATENT DOCUMENTS 5,301,381  4/1994  Klupt ............................................ 15/29

Primary Examiner—Randall E. Chin
Attorney, Agent, or Firm—Jackson Walker L.L.P.

[57] ABSTRACT

An electric toothbrush includes a drive shaft that is reciprocated by a motor in a brush handle (not shown). The reciprocating movement is directly transferred to a piston that serves to pump water from a reservoir via a water passage to a water jet nozzle in the midst of brushes.

4 Claims, 2 Drawing Sheets

TOOTHBRUSH WITH WATER JET

SUMMARY OF THE INVENTION

The invention relates to electric toothbrushes.

The invention relates more particularly to a toothbrush with a water jet. It has already been proposed to use an electric toothbrush that has a removable head and a separate water jet attachment that fits to the handle and receives driving power from the toothbrush motor mounted in the handle. It has also been proposed to have a combined brush head and water jet in which the brush is driven by a motor and the water is separately pumped or pressurised e.g. by a mains supply to exit as a water jet from the brush head. An arrangement has been proposed where separated gears and physically separate pumping devices are used to provide a flow of water to the jet, when required.

It is an object of the invention to provide a combined toothbrush and water jet that is compact and simple in construction.

According to the invention there is provided an electric toothbrush with a water jet, the toothbrush comprising a handle, a shank, and a toothbrush head that incorporates the water jet, in which a motor is mounted in the handle and the toothbrush includes a reciprocating drive shaft extending along the shank to drive brushes in the brush head, including a water passage extending along the shank to connect a water supply to the water jet, and a pump in the shank for pumping water along the passage that is mechanically connected directly to the drive shaft.

The pump preferably comprises a piston that fits around the drive shaft.

The piston may fit in a cylinder that has a water inlet port that is cyclically exposed and closed off in use as the piston is reciprocated by the shaft.

An ON-OFF control knob may be mounted adjacent an end of the shank to open and close a valve connected between the water supply and the water passage.

An electric toothbrush according to the invention will now be described by way of example with reference to the accompanying drawings in which:

DESCRIPTION OF THE PREFERRED EMBODIMENT

Figure 1:
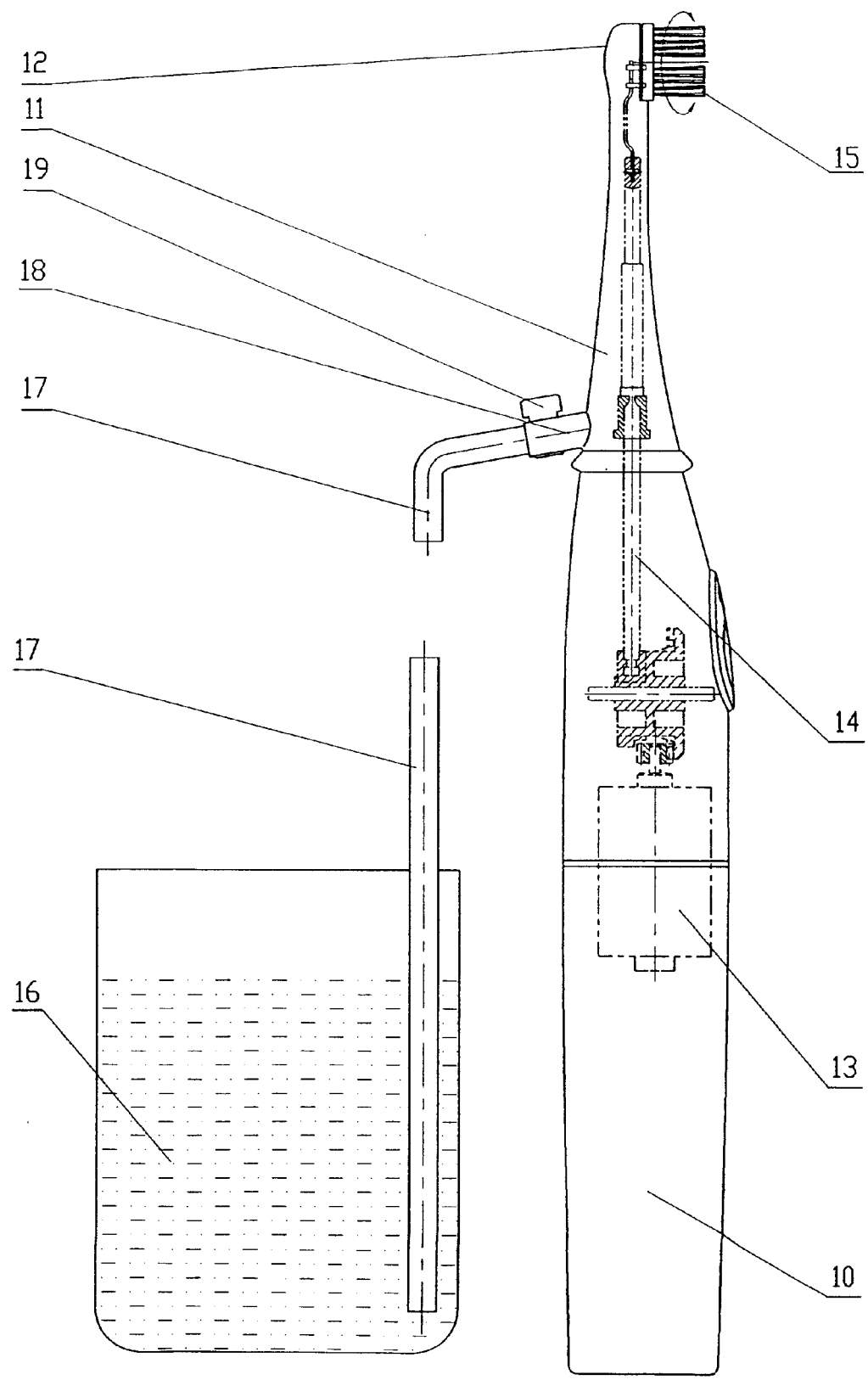
FIG. 1 is an isometric view of the electric toothbrush.

Referring to the drawings, in FIG. 1 the electric toothbrush comprises a handle 10, a shank 11, and a toothbrush head 12. A motor 13 in the handle 10 provides a reciprocating drive to an output shaft 14 to rotate a set of brushes 15 backwards and forwards, as explained in GB Patent No. 283411.

A water reservoir 16 provides a supply of water, or suitable liquid for washing teeth, and a flexible hose 17 connects the water reservoir to a pipe 18 integrally formed at one end of the shank 11. An ON-OFF control knob 19 is provided for opening and closing a valve in the pipe 18.

Figures 2, 3:
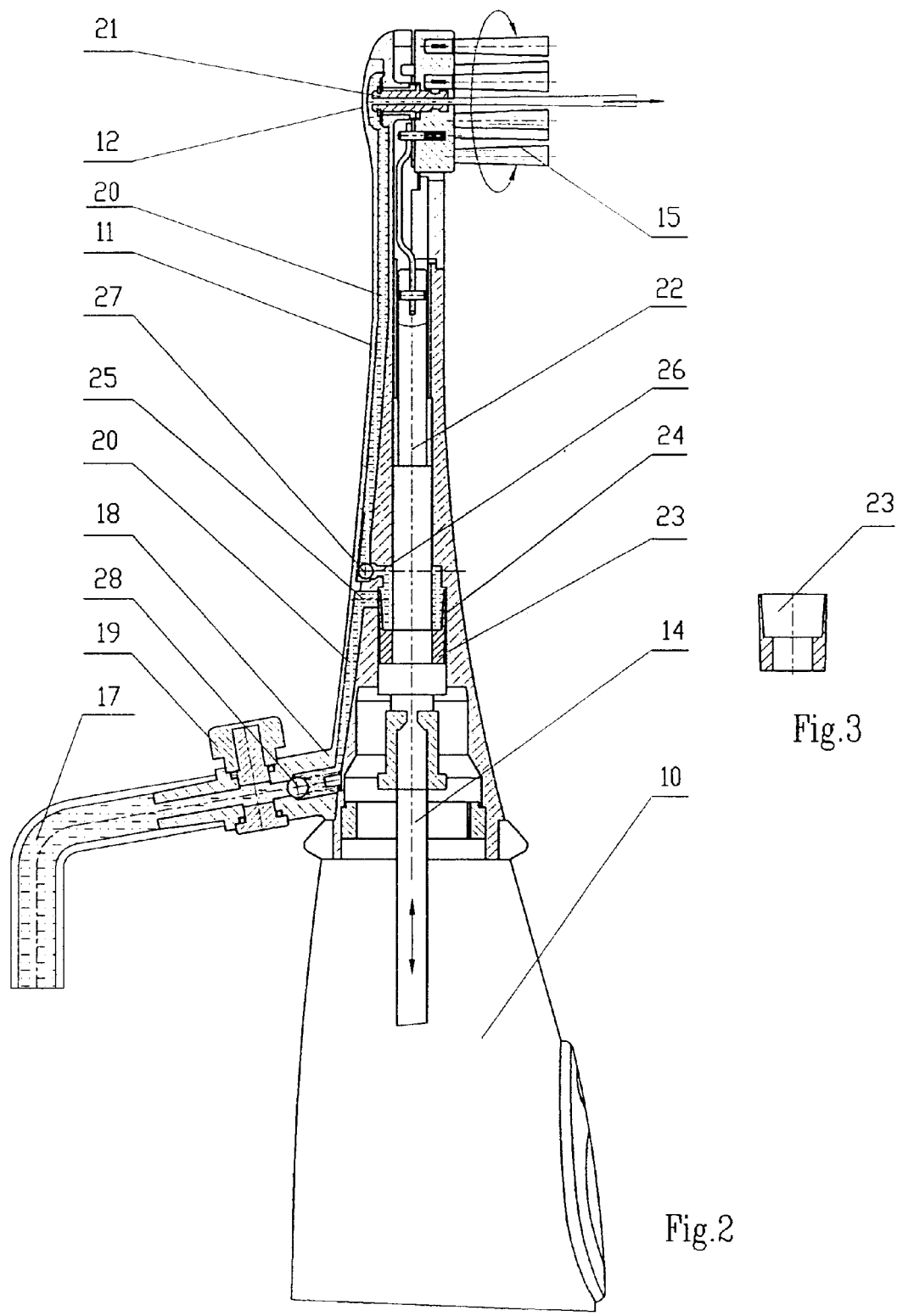
FIG. 2 shows a cross-section of part of the toothbrush.
FIG. 3 shows a cross-section of a piston incorporated in the toothbrush.

In FIG. 2, a water passage 20 extends along the shank to connect the water reservoir to a water jet nozzle 21 that, in use, provide a spray of water between the brushes 15, when required, to rinse a user's teeth and mouth. A drive shaft 22 extends along the shank 11 and is connected to the output shaft 14 to transfer reciprocating motion to the brush head 12 for driving the brushes 15.

A piston 23, better shown in FIG. 3, is directly coupled to and surrounds the shaft 22 for sliding inside a cylinder 24. An inlet port 25 for the cylinder is positioned to be cyclically exposed and closed off by a forward end of the piston 23 as the piston reciprocates in the cylinder 24. In FIG. 2, the port 25 is shown closed off and the piston 23 is in its most forward position. An outlet port 26, including an outlet valve 27 that prevents flow of water in a direction towards the cylinder 24, is provided in the passage 20. The pumping parts of the toothbrush are completed by a one-way valve 28 in the tube 18 that prevents flow of water away from the cylinder 24.

In use, when it is required to rinse or provide cleaning or cleansing liquid to the brush head 12 for spraying on to the teeth or into a mouth of a user, the knob is used to turn ON the liquid supply. Normal reciprocating of the shaft 22 then causes the liquid to be sprayed out of the nozzle 21. The pumping action makes direct use of the reciprocating movement of the shaft 22 and the piston 23 and the cylinder 24 fit conveniently and compactly within the shank 11. Furthermore, the piston 23 and the cylinder are relative simple components, conveniently made of molded plastics, that add very little cost to the overall price of the toothbrush or difficulty to its manner of assembly.

I claim:

1. An electric toothbrush with a water jet, the toothbrush comprising a handle, a shank, and a toothbrush head that incorporates the water jet, in which a motor is mounted in the handle and the toothbrush includes a reciprocating drive shaft extending along the shank to drive brushes in the brush head, including a water passage extending along the shank to connect a water supply to the water jet, and a pump in the shank for pumping water along the passage that is mechanically connected directly to the drive shaft.

2. An electric toothbrush according to claim 1, in which the pump comprises a piston that fits around the drive shaft.

3. An electric toothbrush according to claim 2, in which the piston fits in a cylinder that has a water inlet port that is cyclically exposed and closed off in use as the piston is reciprocated by the shaft.

4. An electric toothbrush according to claim 1 including an ON-OFF control knob mounted adjacent an end of the shank to open and close a valve connected between the water supply and the water passage.

* * * * *